(12) United States Patent
Wenkebach et al.

(10) Patent No.: US 6,820,613 B2
(45) Date of Patent: Nov. 23, 2004

(54) PROCESS AND DEVICE FOR CONTROLLING THE BREATHING GAS SUPPLY

(75) Inventors: Ullrich Wenkebach, Lübeck (DE); Dieter Weismann, Gross Grönau (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 0 days.

(21) Appl. No.: 10/390,408

(22) Filed: Mar. 17, 2003

(65) Prior Publication Data

US 2003/0196663 A1 Oct. 23, 2003

(30) Foreign Application Priority Data

Apr. 20, 2002 (DE) .......................................... 102 17 762

(51) Int. Cl.⁷ ............................................ A61M 15/00
(52) U.S. Cl. ............................. 128/200.24; 128/204.21; 128/204.23
(58) Field of Search ....................... 128/200.24, 204.21, 128/204.23; 600/533

(56) References Cited

U.S. PATENT DOCUMENTS

| | | | | |
|---|---|---|---|---|
| 3,036,569 A | * | 5/1962 | Clements et al. | 600/533 |
| 3,621,833 A | * | 11/1971 | Crane | 600/533 |
| 3,713,436 A | * | 1/1973 | Hardway, Jr. | 600/533 |
| 3,902,481 A | * | 9/1975 | Bargeton et al. | 600/533 |
| 4,005,702 A | * | 2/1977 | Bargeton et al. | 600/533 |
| 4,022,193 A | * | 5/1977 | Franetzki et al. | 600/533 |
| 4,031,885 A | * | 6/1977 | Davis et al. | 600/533 |
| 4,036,221 A | * | 7/1977 | Hillsman et al. | 128/204.23 |
| 4,036,222 A | * | 7/1977 | Gillard et al. | 600/533 |
| 4,351,344 A | * | 9/1982 | Stenzler | 600/533 |
| 5,261,397 A | * | 11/1993 | Grunstein | 128/204.18 |
| 5,316,009 A | * | 5/1994 | Yamada | 600/533 |
| 5,582,182 A | * | 12/1996 | Hillsman | 600/529 |
| 5,876,352 A | * | 3/1999 | Weismann | 600/529 |
| 6,066,101 A | * | 5/2000 | Johnson et al. | 600/533 |

FOREIGN PATENT DOCUMENTS

DE      198 08 543      11/1998

\* cited by examiner

Primary Examiner—Aaron J. Lewis
(74) Attorney, Agent, or Firm—McGlew and Tuttle, P.C.

(57) ABSTRACT

A process is provided for controlling at least one parameter of the breathing gas supply of a respirator with a patient connected to it as well as to a corresponding control device. The respiration pressure, the breathing gas flow generated by the respirator as well as the respiration rate may be used as parameters. The process presents the advantage that the control of the current respiration needs of the patient are taken into account by the muscle pressure ($P_{MUS}$), i.e., the percentage of the airway pressure caused by the patient's own effort, being maintained at a value close to zero. An airway pressure ($P_{AW_C}$) is first calculated for this purpose from previously measured values for the airway pressure ($P_{AW}$) and the breathing gas flow (d/dt V) and the mechanical parameters resistance ($R_L$) and compliance (C) of the patient's lungs, which were determined therefrom, and this is subsequently compared with the actually measured value for the airway pressure ($P_{AW}$). The at least one parameter of the breathing gas supply of the respirator is subsequently controlled on the basis of the comparison between $P_{AW_C}$ and $P_{AW}$, expressed as the muscle pressure $P_{MUS}=P_{AW_C}-P_{AW}$.

9 Claims, 1 Drawing Sheet

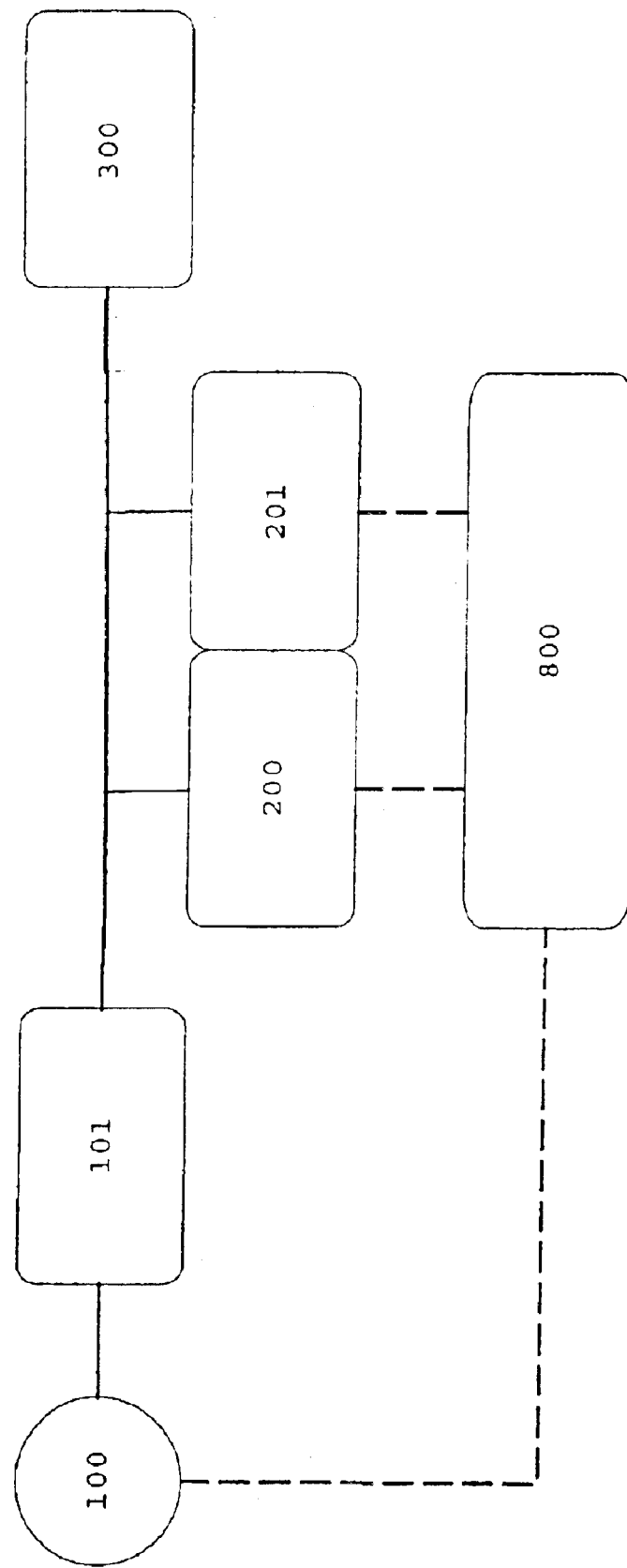

PROCESS AND DEVICE FOR CONTROLLING THE BREATHING GAS SUPPLY

FIELD OF THE INVENTION

The present invention pertains to a process for controlling at least one parameter of the breathing gas supply of a respirator with a patient connected to it as well as to a corresponding control device.

BACKGROUND OF THE INVENTION

The parameters of breathing gas supply by the respirator, e.g., the respiration pressure, the breathing gas flow or the respiration rate, are usually set in advance and are then checked for their validity at greater time intervals. If the patient's respiration need changes, this is then taken into account during the treatment when the parameters of the breathing gas supply are correspondingly adapted after a recent check of the respiration need. A breathing gas supply is therefore obtained that may not be oriented uninterruptedly on the patient's current needs.

DE 198 08 543 C2 discloses a process by which the mechanical properties compliance, resistance and, finally, the muscle pressure of the respiratory system of a patient can be determined during both spontaneous breathing and mechanical respiration, and the patient's breathing is disturbed only minimally. The compliance is the quotient of the displaced breathing gas volume and the change in the airway pressure, and the resistance is the quotient of the change of the airway pressure and the change in the breathing gas flow. The muscle pressure is defined as the percentage of the airway pressure caused by the patient's own effort. This process makes it possible to perform the continuous determination of the muscle pressure of the patient and thus to monitor the intensity of his spontaneous breathing. An occlusion, during which the respiration or spontaneous breathing of the patient is interrupted by closing corresponding valves on a respiration tube leading to the patient, is brought about for this purpose for a short time at different points in time during the individual breathing strokes. The mechanical properties of the lungs can be determined from the measured values for the airway pressure and the breathing gas flow. The muscle pressure is in turn determined from these variables.

SUMMARY OF THE INVENTION

The object of the present invention is to provide a process as well as a device for controlling at least one parameter of the breathing gas supply for a patient, which takes into account the current state of his respiratory system.

According to the present invention, the measured values for the airway pressure, $P_{AW}$, and the breathing gas flow, d/dt V, are used continuously for the determination of the mechanical properties of the patient's respiratory system, i.e., the resistance $R_L$ and the compliance C of his lungs, and, finally for the determination of the muscle pressure $P_{MUS}$.

According to the invention, a process is provided for controlling at least one parameter of the breathing gas supply of a respirator with a patient connected to it. With a brief disturbance of the breathing gas supply taking place during a first phase of expiration, the airway pressure $P_{AW}$ and the breathing gas flow d/dt V are measured before and during the disturbance, and the resistance $R_L$ of the patient's lungs is determined as the quotient of the airway pressure $P_{AW}$ and the change in the breathing gas flow d/dt V. The airway pressure $P_{AW}$ and the breathing gas flow d/dt V are measured during a second, undisturbed phase of expiration, and the compliance C of the patient's lungs is determined from this as well as from the resistance $R_L$. The breathing gas flow d/dt V is measured each time during the subsequent breaths, and an airway pressure $P_{AW_C}$ is calculated from this together with the resistance $R_L$ and the compliance C. A muscle pressure $P_{MUS}$ is determined as the difference between the calculated airway pressure $P_{AW_C}$ and the actually measured airway pressure $P_{AW}$. The at least one parameter of the breathing gas supply is changed such that the breathing gas supply is increased during the further phases of inspiration when the muscle pressure $P_{MUS}$ is above a set point $P_0$, and the at least one parameter of the breathing gas supply is changed such that the breathing gas supply is reduced during the subsequent phases of inspiration when the muscle pressure $P_{MUS}$ is below the set point $P_0$ until the muscle pressure $P_{MUS}$ reaches the set point $P_0$.

According to another aspect of the invention a device is provided for controlling at least one parameter of the breathing gas supply of a respirator with a patient connected to it. The device includes means designed to bring about a brief disturbance in the breathing gas supply during a phase of expiration. A first sensor is provided for measuring the airway pressure $P_{AW}$ and a second sensor is provided for measuring the breathing gas flow d/dt V. An evaluating and control unit is provided for determining the resistance $R_L$ and the compliance C of the patient's lungs from the airway pressure $P_{AW}$ measured by the first sensor and the breathing gas flow d/dt V measured by the second sensor, for calculating an airway pressure $P_{AW_C}$ from the resistance $R_L$, the compliance C and the measured breathing gas flow d/dt V, and for determining a muscle pressure $P_{MUS}$ as the difference between the calculated airway pressure $P_{AW_C}$ and the actually measured airway pressure $P_{AW}$. The at least one parameter of the breathing gas supply is changed by the evaluating and control unit such that the breathing gas supply is increased during the subsequent phases of inspiration when the muscle pressure $P_{MUS}$ is above a set point $P_0$, and the at least one parameter of the breathing gas supply is changed by the evaluating and control unit such that the breathing gas supply is reduced during the subsequent phases of inspiration when the muscle pressure $P_{MUS}$ is below the set point $P_0$ until the muscle pressure $P_{MUS}$ reaches the set point $P_0$.

According to another aspect of the invention a process is provided for controlling at least one parameter of the breathing gas supply of a respirator with a patient connected to it. The airway pressure $P_{AW}$ and the breathing gas flow d/dt V are measured in a plurality of phases of expiration, and the resistance $R_L$ and the compliance C of the patient's lungs are determined from this. The breathing gas flow d/dt V is measured during subsequent breaths and an airway pressure $P_{AW_C}$ is calculated from this together with the resistance $R_L$ and the compliance C. A muscle pressure $P_{MUS}$ is determined as the difference between the calculated airway pressure $P_{AW_C}$ and the actually measured airway pressure $P_{AW}$. The at least one parameter of the breathing gas supply is changed such that the breathing gas supply is increased during the subsequent phases of inspiration when the muscle pressure is above a set point $P_0$, and the at least one parameter of the breathing gas supply is changed such that the breathing gas supply is reduced during the subsequent phases of inspiration when the muscle pressure $P_{MUS}$ is below the set point $P_0$ until the muscle pressure $P_{MUS}$ reaches the set point.

In the process for controlling at least one parameter of the breathing gas supply of a respirator with a patient connected to it, the breathing gas supply is briefly disturbed during a first phase of expiration. The airway pressure PAW and the breathing gas flow d/dt V are measured before and during the disturbance. The resistance $R_L$ of the patient's lungs is determined from this. The airway pressure PAW and the breathing gas flow d/dt V are likewise measured during a second, undisturbed phase of expiration. The compliance C of the patient's lungs is determined from these values as well as the resistance $R_L$ determined in the preceding step.

The breathing gas flow d/dt V is measuring during the subsequent breaths. Together with the values determined before for the resistance $R_L$ and the compliance C, an airway pressure $PAW_C$ is calculated from this.

The muscle pressure PMUS, i.e., the percentage of the airway pressure caused by the patient's own effort, is subsequently determined as the difference from the calculated airway pressure $PAW_C$ and the actually measured airway pressure PAW. The control proper is now performed as a function of the muscle pressure PMUS determined. The at least one parameter of the breathing gas supply is now changed such that the breathing gas supply is increased during the subsequent phases of inspiration when the muscle pressure PMUS is above a set point $P_0$, and the at least one parameter of the breathing gas supply is changed such that the breathing gas supply is reduced during the subsequent phases of inspiration when the muscle pressure PMUS is below the set point $P_0$ until the muscle pressure PMUS reaches the set point $P_0$.

If, e.g., a positive value is thus obtained for PMUS during the phases of inspiration and a PMUS value close to zero is obtained during the phases of expiration, this indicates that a higher respiration pressure or breathing gas flow is necessary for an increased breathing gas supply. If, moreover, PMUS is already positive before the beginning of a phase of inspiration, an increase in the respiration rate may be expedient.

In a preferred embodiment of the process, the at least one parameter is the respiration pressure, i.e., the airway pressure generated by the respirator. Moreover, the breathing gas flow generated by the respirator as well as the respiration rate preset by the respirator may be used as parameters. The brief disturbance in the breathing gas supply of the patient may be an occlusion of the patient's airways, but also a change in the respiration pressure.

The device according to the present invention for controlling at least one parameter of the breathing gas supply of a respirator with a patient connected to it is designed to bring about a brief disturbance in the breathing gas supply during a phase of expiration. It has a first sensor for measuring the airway pressure PAW and a second sensor for measuring the breathing gas flow d/dt V. Moreover, an evaluating and control unit is used to determine the resistance $R_L$ and the compliance C of the patient's lungs from the airway pressure PAW measured by the first sensor and the breathing gas flow d/dt V measured by the second sensor. The evaluating and control unit calculates an airway pressure $PAW_C$ from further measured values for the breathing gas flow d/dt V as well as from the resistance $R_L$ determined previously and the compliance C. Finally, the muscle pressure PMUS, i.e., the percentage of the airway pressure caused by the patient's own effort, is determined. It is determined by the evaluating and control unit as the difference between the calculated airway pressure $PAW_C$ and the actually measured airway pressure PAW. The evaluating and control unit then changes the at least one parameter of the breathing gas supply in the manner already described above.

The disturbance in a phase of expiration of the patient is always brief if possible and is, e.g., in the range of a few hundred msec, preferably about 200 msec, in order not to compromise the patient's respiration. The disturbances are performed in a sequence following a chronological pattern and occur, e.g., once or several times per minute. It is advantageous in this connection to induce the individual disturbances at different points in time relative to the individual phases of expiration, because the reliability of the measurements is increased by this scattering.

The present invention utilizes the situation that the muscle pressure PMUS is a meaningful value when information is to be obtained on the patient's respiratory efforts. If the muscle pressure PMUS is maintained at a preset value, which is usually zero or very low in practice, it is guaranteed in this manner that the patient must make only little respiratory effort of his own and the so-called "ventilator fighting" is avoided.

It will be described below how the resistance $R_L$ and the compliance C of the patient's lungs are determined from the measured values for the airway pressure PAW and the breathing gas flow d/dt V and, finally, how the muscle pressure PMUS is determined.

The starting point is the following basic equation:

$$PMUS = \frac{1}{C} \cdot V + R_L \cdot d/dt\, V - PAW + PEEP_t,$$

in which V designates the displaced breathing gas volume. $PEEP_t = PEEP_{IN} + PEEP_{EX}$ is the total positive end expiratory pressure, which is composed of the intrinsic $PEEP_{IN}$, which results from the gas volume left in the patient's lungs after complete expiration, and the external $PEEP_{EX}$, which is predetermined by the respirator. (For dividing the total $PEEP_t$ into the two components $PEEP_{IN}$ and $PEEP_{EX}$, see, e.g., U.S. Pat. No. 6,015,388.)

The resistance $R_L$ is first determined as a quotient of the difference of two measured airway pressures $P_{AW1}$ and $P_{AW2}$ and the difference of two breathing gas flows measured at the same points in time $(d/dt\, V)_1$ and $(d/dt\, V)_2$:

$$R_L = \frac{PAW1 - PAW2}{(d/dt\, V)1 - (d/dt\, V)2}.$$

The $P_{AW1}$ and $(d/dt\, V)_1$ measurements are performed before and the $P_{AW2}$ and $(d/dt\, V)_2$ measurements during a brief disturbance in a phase of expiration. If the disturbance is an occlusion, the breathing gas flow $(d/dt\, V)_2$ becomes zero, and the following is obtained for the resistance $R_L$ of the lungs:

$$R_L = \frac{PAW1 - PAW2}{(d/dt\, V)1}$$

The external resistance $R_{ex}$ and the external $PEEP_{ex}$ are then determined from the following equation:

$$P_{AW} = -R_{ex} \cdot d/dt\, V + PEEP_{EX}.$$

The external resistance $R_{ex}$ is the resistance caused by the resistance in the expiration branch of the respirator, which forms the total resistance of the patient's lungs together with the resistance $R_L$.

The above equation is based on the basic equation for the special case of an expiration. By performing at least two measurements for the airway pressure P$_{AW}$ and the breathing gas flow d/dt V, a sufficient number of equations are obtained for determining the external resistance R$_{ex}$ and the external PEEP$_{EX}$.

The more measurements that are carried out, the better are the possibilities to obtain reliable values for R$_{ex}$ and the external PEEP$_{EX}$ with approximation methods.

The following equation applies to the breathing gas flow d/dt V and the breathing gas volume V$_{EX}$ displaced during an expiration:

$$d/dtV = -\frac{1}{\tau}V_{ex} + (d/dt\ V)_{t0}$$

with the expiration time constant $\tau$ and an initial value (d/dt V)$_{t0}$ at the time t$_0$.

Several measurements of the breathing gas flow d/dt V lead to a sufficient number of equations for determining the expiration time constant $\tau$ and the initial value (d/dt V)$_{t0}$ here. As in the case above, approximation solutions of a higher reliability can be determined with additional measurements. The compliance C can now be determined based on the equation $$C = \frac{\tau}{Rex + RL}.$$

The intrinsic PEEP$_{IN}$ is obtained from $$PEEP_{IN} = \frac{1}{C}(\tau \cdot (d/dt\ V)_{t0} - V_{ee}) - PEEP_{EX},$$

in which V$_{ee}$ is a breathing gas volume displaced during a complete expiration. The term $\tau \cdot$(d/dt V)$_{t0}$-V$_{ee}$ designates the so-called hyperinflation volume.

It is possible at this point to calculate an airway pressure P$_{AW_C}$ using the variables determined before and with additional measured values for the breathing gas flow d/dt V. In addition, a value is obtained for the airway pressure P$_{AW}$ by measurement. The muscle pressure P$_{MUS}$ is obtained as the difference between the calculated and measured airway pressures:

$$P_{MUS} = P_{AW_C} - P_{AW}.$$

The calculation steps indicated here, which lead to a value for P$_{MUS}$, have the character of an example. The basic principle of the process according to the present invention, which is also used in modified calculation steps, is the calculation of an airway pressure P$_{AW_C}$ from the previously measured values for the airway pressure P$_{AW}$ and the breathing gas flow d/dt V and the mechanical parameters of the patient's respiratory system, which were determined therefrom, the subsequent comparison with an actually measured value for the airway pressure P$_{AW}$ and, finally, the control on the basis of a comparison between two values, expressed as the muscle pressure P$_{MUS}$.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The FIGURE shows a respirator, with which the process according to the present invention can be carried out.

DESCRIPTION OF THE PREFERRED EMBODIMENT

Referring to the drawings in particular, the FIGURE shows a respirator, with which the process according to the present invention can be carried out. A ventilator 100 supplies a patient 300 connected to the respirator with breathing gas. A brief disturbance in the breathing gas supply, brought about, e.g., by occlusion of the airways, is carried out by a disturbance device or disturbing means 101 in the expiration branch of the respirator. A first sensor 200, which measures the airway pressure P$_{AW}$, is arranged in the respirator. The breathing gas flow d/dt V is measured by a second sensor 201, which is likewise arranged in the respirator. The values measured by the first sensor 200 and the second sensor 201 are sent to an evaluating and control unit 800. The resistance R$_L$ and the compliance C of the patient's lungs are first calculated there from the measured values, and the airway pressure P$_{AW_C}$ is subsequently calculated. The evaluating and control unit 800 compares the calculated airway pressure P$_{AW_C}$ with the airway pressure P$_{AW}$ actually measured by the first sensor 200. If the muscle pressure P$_{MUS}$=P$_{AW_C}$–P$_{AW}$ is positive, the ventilator 100 is actuated by the evaluating and control unit 800 such that the respiration pressure is increased. If P$_{MUS}$=P$_{AW_C}$–P$_{AW}$ is negative, the respiration pressure generated by the ventilator 100 is reduced. The respiration pressure is maintained only when the muscle pressure P$_{MUS}$ is close to zero.

While specific embodiments of the invention have been shown and described in detail to illustrate the application of the principles of the invention, it will be understood that the invention may be embodied otherwise without departing from such principles.

What is claimed is:

1. A process for controlling at least one parameter of the breathing gas supply of a respirator with a patient connected to it, the process comprising:

providing a brief disturbance of the breathing gas supply during a first phase of expiration;

measuring the airway pressure (P$_{AW}$) and the breathing gas flow (d/dt V) before the disturbance;

measuring the airway pressure (P$_{AW}$) and the breathing gas flow (d/dt V) during the disturbance;

determining the resistance (R$_L$) of the patient's lungs as the quotient of the airway pressure (P$_{AW}$) and the change in the breathing gas flow (d/dt V);

measuring the airway pressure (P$_{AW}$) and the breathing gas flow (d/dt V) during a second undisturbed phase of expiration;

determining the compliance (C) of the patient's lungs from the measuring of the airway pressure (P$_{AW}$) and the breathing gas flow (d/dt V) during a second undisturbed phase of expiration as well as from the resistance (R$_L$);

measuring the breathing gas flow (d/dt V) each time during a plurality of subsequent breaths;

calculating an airway pressure (P$_{AW_C}$) from the measuring of the breathing gas flow (d/dt V) each time during a plurality of subsequent breaths together with the resistance (R$_L$) and the compliance (C);

determining a muscle pressure ($P_{MUS}$) as the difference between the calculated airway pressure ($P_{AW_C}$) and the actually measured airway pressure ($P_{AW}$);

changing at least one parameter of the breathing gas supply such that the breathing gas supply is increased during the further phases of inspiration when the muscle pressure ($P_{MUS}$) is above a set point ($P_0$), and the at least one parameter of the breathing gas supply is changed such that the breathing gas supply is reduced during the subsequent phases of inspiration when the muscle pressure ($P_{MUS}$) is below the set point ($P_0$) until the muscle pressure ($P_{MUS}$) reaches the set point ($P_0$).

2. A process in accordance with claim 1, wherein the at least one parameter is the airway pressure generated by the respirator.

3. A process in accordance with claim 1, wherein the at least one parameter is the breathing gas flow (d/dt V) generated by the respirator.

4. A process in accordance with claim 1, wherein the at least one parameter is the respiration rate predetermined by the respirator.

5. A process in accordance with claim 1, wherein the brief disturbance is brought about by an occlusion of patient airways.

6. A process in accordance with claim 1, wherein the brief disturbance is brought about by a change in the respiration pressure.

7. A process in accordance with claim 1, wherein the brief disturbances are carried out according to a chronological pattern according to which they are induced at different points in time relative to the individual phase of expiration.

8. A device for controlling at least one parameter of the breathing gas supply of a respirator with a patient connected to it, the device comprising:

a disturbance device to bring about a brief disturbance in the breathing gas supply during a phase of expiration;

a first sensor for measuring the airway pressure ($P_{AW}$);

a second sensor for measuring the breathing gas flow (d/dt V);

an evaluating and control unit for determining the resistance ($R_L$) and the compliance (C) of the patient's lungs from the airway pressure ($P_{AW}$) measured by the first sensor and the breathing gas flow (d/dt V) measured by the second sensor and for calculating an airway pressure ($P_{AW_C}$) from the resistance ($R_L$), the compliance (C) and the measured breathing gas flow (d/dtV), and for determining a muscle pressure ($P_{MUS}$) as the difference between the calculated airway pressure ($P_{AW_C}$) and the actually measured airway pressure ($P_{AW}$), the at least one parameter of the breathing gas supply being changed by the evaluating and control unit such that the breathing gas supply is increased during the subsequent phases of inspiration when the muscle pressure ($P_{MUS}$) is above a set point ($P_0$), and the at least one parameter of the breathing gas supply is changed by the evaluating and control unit such that the breathing gas supply is reduced during the subsequent phases of inspiration when the muscle pressure ($P_{MUS}$) is below the set point ($P_0$) until the muscle pressure ($P_{MUS}$) reaches the set point ($P_0$).

9. A process for controlling at least one parameter of the breathing gas supply of a respirator with a patient connected to it, the process comprising:

measuring the airway pressure ($P_{AW}$) and the breathing gas flow (d/dt V) in a plurality of phases of expiration;

determining the resistance ($R_L$) and the compliance (C) of the patient's lungs from the measuring of the airway pressure ($P_{AW}$) and the breathing gas flow (d/dt V) in a plurality of phases of expiration;

measuring the breathing gas flow (d/dt V) during subsequent breaths;

calculating an airway pressure ($P_{AW_C}$) together with the resistance ($R_L$) and the compliance (C) from the measuring of the breathing gas flow (d/dt V) during subsequent breaths;

determining a muscle pressure ($P_{MUS}$) as the difference between the calculated airway pressure ($P_{AW_C}$) and the actually measured airway pressure ($P_{AW}$);

changing the at least one parameter of the breathing gas supply such that the breathing gas supply is increased during the subsequent phases of inspiration when the muscle pressure is above a set point ($P_0$), and the at least one parameter of the breathing gas supply is changed such that the breathing gas supply is reduced during the subsequent phases of inspiration when the muscle pressure ($P_{MUS}$) is below the set point ($P_0$) until the muscle pressure ($P_{MUS}$) reaches the set point.

* * * * *